United States Patent
Sund et al.

(10) Patent No.: US 11,660,226 B2
(45) Date of Patent: *May 30, 2023

(54) OSTOMY APPLIANCE HAVING AN ADHESIVE WAFER WITH SENSING MEANS

(71) Applicant: Coloplast A/S, Humlebaek (DK)

(72) Inventors: Anders Grove Sund, Alleroed (DK); Lasse Hylleberg Mølleskov, Copenhagen (DK); Esben Strøbech, Hoersholm (DK)

(73) Assignee: Coloplast A/S, Humlebaek (DK)

( * ) Notice: Subject to any disclaimer, the term of this patent is extended or adjusted under 35 U.S.C. 154(b) by 255 days.

This patent is subject to a terminal disclaimer.

(21) Appl. No.: 16/916,111

(22) Filed: Jun. 30, 2020

(65) Prior Publication Data
US 2020/0330259 A1 Oct. 22, 2020

Related U.S. Application Data

(62) Division of application No. 14/905,812, filed as application No. PCT/DK2014/000038 on Jul. 15, 2014, now Pat. No. 10,736,769.

(30) Foreign Application Priority Data

Jul. 18, 2013 (DK) .............................. PA 2013 70407
Jun. 12, 2014 (DK) .............................. PA 2014 70351

(51) Int. Cl.
*A61F 5/443* (2006.01)
*A61F 5/44* (2006.01)
*A61F 5/445* (2006.01)
*A61F 5/448* (2006.01)

(52) U.S. Cl.
CPC ............ *A61F 5/4404* (2013.01); *A61F 5/443* (2013.01)

(58) Field of Classification Search
CPC .......... A61F 5/443; A61F 5/4404; A61F 5/44; A61F 5/4405; A61F 5/4401; A61F 5/445; A61F 5/448; A61F 2005/4455
See application file for complete search history.

(56) References Cited

U.S. PATENT DOCUMENTS

| | | | | |
|---|---|---|---|---|
| 5,942,186 A | * | 8/1999 | Sanada | A61F 5/443 436/63 |
| 7,105,715 B2 | * | 9/2006 | Carlucci | A61F 13/42 604/385.01 |
| 7,260,999 B2 | * | 8/2007 | Divigalpitiya | H01H 1/029 73/774 |
| 7,483,731 B2 | * | 1/2009 | Hoarau | A61B 5/14552 600/323 |
| 7,737,321 B2 | * | 6/2010 | Elliott | A61F 5/445 604/277 |
| 8,398,603 B2 | * | 3/2013 | Thirstrup | A61B 5/746 602/41 |
| 9,066,812 B2 | * | 6/2015 | Edvardsen | A61F 5/443 |
| 10,736,769 B2 | * | 8/2020 | Grove Sund | A61F 5/4404 |
| 2002/0192829 A1 | * | 12/2002 | Zainiev | A61F 13/72 436/39 |
| 2004/0078219 A1 | * | 4/2004 | Kaylor | G16H 40/67 600/300 |
| 2008/0275327 A1 | * | 11/2008 | Faarbaek | A61B 5/68335 600/382 |
| 2009/0204100 A1 | * | 8/2009 | Van Pieterson | A61B 5/01 600/549 |
| 2009/0234312 A1 | * | 9/2009 | O'Toole | A61F 5/448 604/332 |
| 2010/0030167 A1 | * | 2/2010 | Thirstrup | A61F 5/4404 340/657 |
| 2011/0106032 A1 | * | 5/2011 | Kratky | A61F 5/445 604/337 |
| 2011/0319787 A1 | * | 12/2011 | Lamoise | A61B 5/103 600/587 |
| 2012/0143154 A1 | * | 6/2012 | Edvardsen | A61F 5/4404 604/336 |
| 2012/0143155 A1 | * | 6/2012 | Edvardsen | A61F 5/443 604/318 |
| 2016/0151196 A1 | * | 6/2016 | Grove Sund | A61F 5/4404 604/318 |
| 2020/0330259 A1 | * | 10/2020 | Sund | A61F 5/4404 |

FOREIGN PATENT DOCUMENTS

WO   WO-2011003420 A1 *   1/2011   ............ A61F 5/4404

* cited by examiner

*Primary Examiner* — Guy K Townsend
(74) *Attorney, Agent, or Firm* — Coloplast Corp., Coloplast A/S; Nick Baumann

(57) ABSTRACT

An ostomy appliance has an adhesive wafer with a backing layer and an adhesive layer attached to the backing layer. The adhesive wafer has sensing means capable of recording application of pressure to the adhesive wafer during application of the ostomy appliance to the skin.

24 Claims, No Drawings

OSTOMY APPLIANCE HAVING AN ADHESIVE WAFER WITH SENSING MEANS

The invention relates to a method of monitoring the pressure applied to an ostomy appliance during application to the skin. The invention further relates to ostomy appliances with means for monitoring the pressure applied to an ostomy appliance during application to the skin.

BACKGROUND

In connection with surgery for a number of diseases in the gastro-intestinal tract, one of the consequences in many cases is that the patient is left with an abdominal stoma, such as a colostomy, an ileostomy or a urostomy in the abdominal wall for the discharge of visceral contents. The discharge of visceral contents cannot be regulated at will. For that purpose, the user will have to rely on an appliance to collect the material emerging from such opening in a bag, which is later emptied and/or discarded at a suitable time.

An ostomy appliance may be in the form of a one-piece appliance for which a collecting bag for human body wastes is permanently, or fixedly, secured to an adhesive base plate for attachment to the human skin. Alternatively, the ostomy appliance may be a two-piece appliance comprising a base plate and a collecting bag which may be coupled to and un-coupled from each other through a coupling means. This has the effect that the base plate does not need to be separated from the skin of the user as often as exchange of the collecting bag requires. The base plate may need only to be changed every third or fourth day depending on the user, whereas the collecting bag may be changed more than once per day. Typically, it is desirable to need as few exchanges of the base plate as possible in order to reduce the risk of skin complications.

One of the main concerns of ostomates using ostomy appliances having an adhesive base plate for attachment to the skin surrounding a stoma, and where a collecting bag is attached to the base plate for collecting stoma output, is leakage or even complete detachment of the ostomy appliance.

Numerous attempts have been made to solve this problem and even though some attempts have been partly successful, still there exist no products that completely solve this problem.

One reason why this is so difficult to solve is the fact that stomas and peoples anatomy are very different. Different considerations need to be made for thin people than for larger people, for different skin types, for placement of the stoma which may vary a lot from person to person, for scar tissue surrounding the stoma, local irregular skin topography, e.g. a hernia, and more—and in particular combinations of all of the above.

Another reason may be the way the adhesive wafer is applied to the skin surrounding the stoma. If the wafer is not sufficiently fixed to the skin due to carelessness or inattentive application, leaks may occur. The adhesive used for ostomy appliances are typically pressure sensitive adhesives, meaning that application of pressure to the adhesive enhances the adhesive tack of the adhesive, thus it attaches better to the skin. In several cases, ostomy bag users do not apply pressure enough to the adhesive base plate of the bag sufficiently to maintain the adhesive capabilities as well as they may neglect to apply pressure over the entire wafer, due to carelessness or reduced dexterity of the user's hands. This may cause leakage from the stoma.

This problem has been tried solved by using a stronger adhesive, but this may give rise to other problems, as this is more aggressive to the skin and more difficult to remove from the skin. Furthermore, a stronger adhesive may still not be enough, it is equally important that the wafer is mounted sufficiently.

Thus, there is a need to further develop and find improvements in order to solve this problem. In other words, there exists a need to monitor that the ostomy wafer is correctly applied to the user.

SUMMARY OF THE INVENTION

One aspect of the invention is to record the user's pattern of movements during application of an ostomy wafer.

An aspect of the invention is to provide an education tool for (new) users of ostomy appliances.

An aspect is to provide feedback to the user, in order to inform them about where and whether or not they have applied sufficient pressure to the wafer.

DETAILED DESCRIPTION OF THE INVENTION

In a first aspect, the invention relates to a method of monitoring the pressure applied to an ostomy appliance during application to the skin, the ostomy appliance comprising an adhesive wafer comprising a backing layer facing away from the skin and an adhesive layer for attachment to the skin, the method comprising the steps of: providing sensing means capable of recording application of pressure to the wafer, applying the adhesive wafer to the skin surrounding the stoma by applying pressure to the sensing means and wafer and retrieving the recorded data from the sensing means.

The method may serve to help and inform the user during application of the wafer. By the method of the invention, the user is provided with direct feedback to the quality of application process and this may cause the user to be more alert when applying the wafer, knowing which areas of the wafer that are important to address and which areas that may need an extra impact.

The method reveals where the users touch and press the wafer during application to the skin surrounding the stoma. The retrieved data from the application process may disclose that the user fails to attach the entire adhesive surface correctly to the skin and thus teach him to attend these forgotten areas. The adhesive used for such ostomy wafers typically comprises two types of polymers; a tacky polymer and a viscous polymer, and if a user is not thorough enough in pressing the adhesive to the skin during application, it may only be the tacky polymer that is attaching to the body. The method of the invention renders it possible to map where, and how hard the user applies enough pressure—and where not.

The method of the invention renders it possible to measure, monitor and log, where the users touch the wafer when they are applying it. This may be useful information both for the user in the daily care and also for the health care people instructing new users.

The retrieved data from the application process may be used to reconstruct the course of actions. Reconstruction of the applied pressure in a model may help to eliminate or confirm the application of the wafer as an important variable in the search for cause of leakage.

The method and the appliance may be used as an educational tool, to instruct users in how thorough they need to be in application of the wafer. Furthermore, it may be used to gain knowledge from users and where they apply pressure to the wafer and consider this information in further product development.

In a second aspect, the invention relates to an ostomy appliance comprising an adhesive wafer, the wafer comprising a backing layer facing away from the skin and an adhesive layer for attachment to the skin, the wafer comprising a sensing means capable of recording application of pressure to the wafer.

The sensing means may be integrated in the wafer. The sensing means may be in the form of a layer on the non-skin facing surface of the backing layer, or the backing layer or it may be embedded in the adhesive or it may be located between the backing layer and the adhesive.

The sensing means may have a size (area) corresponding to the wafer or smaller. Leakage usually develops from the central portion of the wafer, thus the sensing means may at least cover the central portion of the wafer.

The sensing means may be slightly larger, extending further radially than the wafer, in order to secure the edge portion is fully attached.

The sensing means may be in the form of a separate sheet overlying at least a part of the wafer. When the sensing means are in the form of a sheet on the non-skin facing surface of the backing film, the sheet may be detachable or permanently fixed to the backing layer. The sensing means may be in the form of a separate sheet being attached to a collection bag or the sensing mean may be incorporated in the bag material, or they may be provided inside the bag, in an area overlying at least a part of the wafer. The sheet may be permanently fixed to the bag or it may be detachable. A detachable sheet can be detached and entered into a medical journal or scanned for logging the data. The sensing means may be a part of the bag. The sensing means may be provided with a cover layer overlying at least a part of the non-skin facing surface of the sensing means. Such cover layer may hide the visual reaction on the sensing means until the cover layer is removed.

The pressure sensing means may be a pressure sensitive material developing a color change when exposed to pressure. The color change may occur immediately or within a few minutes after exposure to pressure of a predetermined force. The color reaction may be visible to the user or nurse.

There are several ways of achieving a color reaction as a result of a pressure impact. The pressure sensing material may be in the form of a two polymer sheet material provided with a coating on one or both the sheets. The coating may comprise chemical components that, when brought in direct contact with each other's will develop a color reaction. The coating may for example be in the form of small particles or microcapsules, where the particles or capsules may break and release their content, thereby producing a color reaction, when they are exposed to pressure. Or particles from the coating on one sheet is transferred to the other sheet, thereby producing a visible reaction.

The pressure sensing material may be in the form of a two polymer sheet material having small particles, that changes color, when they are pressed together. A two polymer sheet material that is used to illustrate pressure is placed on the wafer in order to show, where the user has touched the wafer. The two polymer sheets have small particles that changes color, when they are pressed together. Hence, when mounting the wafer the user will get instant visual feedback on whether the adhesive is sufficiently attached to the skin.

In one embodiment, the sensing means may be graphite paper.

The pressure sensing material may develop a change in optical properties/light transmission such that a visual change is observed when the material is exposed to pressure. The sensing means may comprise two layers of film overlying each other's, the first layer being transparent and provided with a rough coating, such as an adhesive layer, facing the second layer. When the layers are overlying each other's they may appear opaque or non-transparent due to the air trapped between the coating and the second layer and some light may be reflected by the coating. When the layers are pressed together, the air is squeezed out and the contact between the layers causes the light to be transmitted through the rough coating and hereby making the two layers appear more transparent/translucent. It is the same effect that appears when a strip of adhesive tape is loosely attached to a surface—the tape will be quite visible due to the air trapped in the rough surface of the adhesive and appear opaque, but when the tape is rubbed with a finger in or der to firmly attach it to the surface, it may become more invisible (transparent/translucent) as the adhesive is forced into direct contact with the surface to which it is applied and the trapped air is squeezed out. Thus, the transmission or reflection of light of the sensing means is altered by application of pressure and the visual appearance of the tape is changed.

The coating or the backing layer may be provided with a tactile structure, such as a pattern coating in order to render the change more visible and/or tactile. The color change may encourage the user to touch and apply pressure the entire wafer. The direct feedback, may be an easy and informative way to let the user know, where the applied pressure and thereby the application of the wafer is (in)sufficient.

The sensing means may be used to reconstruct the application of pressure to the wafer afterwards. The color pattern obtained may be transformed into a three dimensional model or it may be logged in an electronic file.

The two-sheet material using small particles that when they collide and break upon contact/pressure will develop a color change, for example go from colorless to a bright red color. The intensity of the color may depend on the amount of pressure applied and the timeframe of which the pressure is applied. The wafer may be scanned or a photo is taken and the print may be converted into a 3D model and/or logged in the patient's file. The 3D model may give an indication of where the applied pressure was highest/lowest and it may be possible to reconstruct the same pressure using a silicone model.

The pressure sensing means may be a thermochromic material. Such material does not in itself directly respond to pressure, but records changes in temperature. However, the harder and/or longer the fingers are pressed or rubbed against the thermochromic material, the more the temperature will rise and the resulting color reaction will thus indirectly reflect the application of pressure.

Some thermochromic material may be reversible, thus the color will revert to the starting point over time. This opens up for the possibility that the sensing means can be reused. However, the thermochromic material may also be chosen to be non-reversible in order to save the recorded material. The fact that the sheet is responsive to heat, may also have the effect the user is encouraged to heat the wafer even more, which will result in a better adhesion of the wafer.

A heat sensitive sheet changes color due to temperature changes. Such thermochromic sheet may for example be a sheet comprising liquid crystals that change shape when heated and thereby reflect different wavelengths of light—which makes it change color.

Thermochromic polymers may be cast into the wafer or the backing layer of the wafer or the thermochromic polymers may be comprised in a separate sheet overlying at least a part of the wafer. The sheet may be unreleasably attached to the backing layer or it may be releasably attached for example by a weak adhesive.

The pressure sensitive material may be changing color when a predetermined threshold is exceeded. The sensitivity of the pressure sensing means may be adjusted to avoid pressure registration during handling of the wafer before application but only react when the pressure is high enough to have an impact on the adhesion to the skin.

The sensing means may be a pressure sensitive material developing a tactile change when exposed to pressure. This may be advantageous in the case where it is difficult for the user to observe the wafer during application, for example using a one-piece device or in the case of obesity.

The tactile change may be in the form of material that can be flattened, collapsed or displaced. The collapsible area may be the entire wafer surface or it may be a part thereof, for example the central part or in the form of dots or ridges that can be flattened when exposed to pressure.

The pressure sensing means may be in the form of a moldable mass, for example a moldable adhesive. The moldable mass may be provided in a topographical pattern that diminishes or disappear when exposed to pressure. In this way, a tactile response is achieved.

The sensing means may comprise a collapsible foam. The foam may be adapted to collapse when exposed to a predetermined pressure threshold. The threshold may be chosen to be a pressure that is sufficient to attach the adhesive properly and high enough to avoid pressure during the handling of the wafer before application to have impact on the result.

In one embodiment the material may be in the form of multiple gas-filled pockets, like bubble wrap. The pockets may be broken or collapsed when exposed to pressure. The breaking of the pockets may also produce a sound that may help the user to ensure that the applied pressure was high enough. Data may be logged by 3D scanning or by saving the sensing means for the journal.

The sensing means may be a pressure sensitive material developing an electronic impulse when exposed to pressure. The sensing means may be in the form of a separate sheet being attached to a collection bag, in an area overlying at least a part of the wafer. Such sheet may be reusable. In another embodiment, the sensing means are incorporated in the wafer.

Force-sensitive resistors (FSR) are able to record not only where the user applies pressure to the wafer, but also the degree of pressure being applied. Such sensor may be in the form of two layers separated by a conductive sheet. When the layers are pressed closer together the resistance of the sheet decreases, the change in resistance is measured and the signal converted into a data file in the computer. The sensor may define a pattern such as an x- and a y-axis or a bulls-eye pattern facilitating tracking a relatively precise position of the users touch, even with several touches are carried out simultaneously.

An interactive processor that makes it possible to convert any conductive object or surface to a keyboard input may also be used for electronic logging of applied pressure. As the FSR, the data can be logged and stored, and eventually reproduced.

The ostomy appliance may comprise an adhesive wafer. Such wafer may typically comprise a backing layer coated with an adhesive layer. The wafer may comprise an aperture for receiving a stoma or body opening. A collection bag may be connected to the wafer.

The bag may be detachable from the wafer or it may be integrated with the wafer. Such appliances may be two-piece or one-piece appliances. In both types of appliances, an adhesive wafer is attached to the wearer's skin. In case of a one-piece appliance, a receiving member or bag is attached to the adhesive wafer. In case of a two-piece appliance, the adhesive wafer forms part of a body side member and a receiving bag is attached releasably to the body side ostomy member for receiving exudates from the stoma.

The coupling means for use in connection with the present invention may be any suitable coupling means known per se for coupling of ostomy base plates to ostomy collecting bags, e.g. a mechanical coupling such as matching coupling rings such as the coupling rings disclosed in WO 91/01118 and WO 91/01119 or WO 94/18919 or matching flanges for adhesive connection of the type disclosed in U.S. Pat. No. 5,800,415.

In one embodiment the bag is provided with an outlet. The outlet facilitates the bag to be emptied and reused.

The appliance may be provided with more than one type of pressure sensing means, opening up for the possibility of combining two or more of the color changing, tactile or electronic registration means in any suitable manner and this is also a part of the invention.

What is claimed is:

1. An ostomy appliance comprising:
   an adhesive wafer comprising a backing layer and an adhesive layer attached to the backing layer, where the adhesive layer is attachable to skin;
   wherein the adhesive wafer comprises a sensing means capable of recording application of pressure to the adhesive wafer during application of the ostomy appliance to the skin.

2. The ostomy appliance of claim 1, wherein the sensing means is a pressure sensitive material developing a color change when exposed to pressure.

3. The ostomy appliance of claim 1, wherein the sensing means is a pressure sensing material including two polymer sheets comprising particles that changes color when the two polymer sheets are pressed together.

4. The ostomy appliance of claim 1, wherein the sensing means is a thermochromic material.

5. The ostomy appliance of claim 1, wherein the sensing means is a pressure sensitive material adapted to change color when a predetermined pressure applied to the pressure sensitive material is exceeded.

6. The ostomy appliance of claim 1, wherein the sensing means is a pressure sensitive material adapted to develop a tactile change when exposed to pressure.

7. The ostomy appliance of claim 1, wherein the sensing means is a collapsible material.

8. The ostomy appliance of claim 1, wherein the sensing means is a pressure sensitive material adapted to develop an electronic impulse when exposed to pressure.

9. An ostomy appliance comprising:
   an adhesive wafer comprising a backing layer and an adhesive layer attached to the backing layer, where the adhesive layer is attachable to skin around a stoma of a user; and
   a sensor integrated into the adhesive wafer;
   wherein the sensor is adapted to measure pressure applied to the adhesive wafer during application of the adhesive wafer to the skin around the stoma of the user.

10. The ostomy appliance of claim 9, wherein the backing layer has a non-skin facing surface located on a side of the backing layer opposite from the adhesive layer, and the sensor is a sensor layer applied to the non-skin facing surface of the backing layer.

11. The ostomy appliance of claim 9, wherein the sensor is embedded in the adhesive layer.

12. The ostomy appliance of claim 9, wherein the sensor is between the backing layer and the adhesive layer.

13. The ostomy appliance of claim 9, wherein the sensor is adapted to provide feedback informing the user of a location on the adhesive wafer where the pressure applied to the adhesive wafer was insufficient to achieve an adhesive seal to the skin around the stoma of the user.

14. The ostomy appliance of claim 9, wherein the sensor comprises a pressure sensitive material adapted to change color in response to the user pressing on the adhesive wafer.

15. The ostomy appliance of claim 9, wherein the sensor comprises a pressure sensitive material adapted to change color when a predetermined pressure applied to the pressure sensitive material is exceeded.

16. The ostomy appliance of claim 9, wherein the sensor comprises two polymer sheets, with at least one of the two polymer sheets comprising particles that changes color when the two polymer sheets are pressed together.

17. The ostomy appliance of claim 9, wherein the sensor comprises a thermochromic material.

18. The ostomy appliance of claim 9, wherein the sensor comprises a pressure sensitive material adapted to develop a tactile change in response to the user pressing on the adhesive wafer.

19. The ostomy appliance of claim 9, wherein the sensor comprises a ridge that is adapted to collapse in response to the user pressing on the adhesive wafer.

20. The ostomy appliance of claim 9, wherein the sensor comprises a pressure sensitive material adapted to develop an electronic impulse in response to the user pressing on the adhesive wafer.

21. The ostomy appliance of claim 9, wherein the sensor comprises a force sensitive resistor adapted to measure a degree of pressure applied to the adhesive wafer during application of the adhesive wafer to the skin around the stoma of the user.

22. The ostomy appliance of claim 9, wherein the sensor comprises a force sensitive resistor comprising two layers separated by an electrically conductive sheet of material.

23. The ostomy appliance of claim 22, further comprising an interactive processor electrically communicating with the force sensitive resistor, where the interactive processor is adapted to electronically log the measured pressure applied to the adhesive wafer during application of the adhesive wafer to the skin around the stoma of the user.

24. An ostomy appliance comprising:
an adhesive wafer comprising a backing layer and an adhesive layer attached to the backing layer, where the adhesive layer is attachable to skin;
wherein the adhesive wafer comprises means for sensing pressure applied to the adhesive wafer during application of the adhesive wafer to the skin.

* * * * *